US006717373B2

(12) United States Patent
Cash

(10) Patent No.: US 6,717,373 B2
(45) Date of Patent: Apr. 6, 2004

(54) METHOD AND APPARATUS FOR SUPPLYING POWER TO A SOURCE OF ILLUMINATION IN A MICROSCOPE

(75) Inventor: David J. Cash, Kenmore, NY (US)

(73) Assignee: Leica Microsystems Inc., Depew, NY (US)

( * ) Notice: Subject to any disclaimer, the term of this patent is extended or adjusted under 35 U.S.C. 154(b) by 0 days.

(21) Appl. No.: 10/041,055

(22) Filed: Jan. 7, 2002

(65) Prior Publication Data

US 2003/0127992 A1 Jul. 10, 2003

(51) Int. Cl.[7] .................................................. A61B 5/00
(52) U.S. Cl. .................................... 315/291; 315/200 A
(58) Field of Search .......................... 315/241 P, 241 S, 315/200 A, 247, 224, 291, 312, 314, 318; 362/216, 33, 119, 109

(56) References Cited

U.S. PATENT DOCUMENTS 4,638,188 A * 1/1987 Cray .......................... 307/453
6,028,694 A * 2/2000 Schmidt ..................... 359/264
6,238,060 B1 * 5/2001 Bourn et al. ................ 362/216
6,414,437 B1 * 7/2002 Diez et al. ..................... 315/77
6,459,919 B1 * 10/2002 Lys et al. .................. 315/291

* cited by examiner

*Primary Examiner*—Wilson Lee
(74) *Attorney, Agent, or Firm*—Simpson & Simpson, PLLC

(57) ABSTRACT

An apparatus for gradually supplying power to a source of illumination in a microscope, including a power transistor operatively arranged to provide a varying applied voltage to the source of illumination, and, means for biasing the power transistor with a pulse width modulated signal to incrementally increase the applied voltage to the source of illumination in a plurality of discrete steps. The invention also includes a method for gradually supplying power to a source of illumination in a microscope by biasing a power transistor with a pulse width modulated signal to incrementally increase the applied voltage to the source of illumination in a plurality of discrete steps.

13 Claims, 6 Drawing Sheets

METHOD AND APPARATUS FOR SUPPLYING POWER TO A SOURCE OF ILLUMINATION IN A MICROSCOPE

REFERENCE TO COMPUTER PROGRAM LISTING APPENDIX

The present application includes a computer program listing appendix on compact disc. Two duplicate compact discs are provided herewith. Each compact disc contains an ASCII text file of the computer program listing as follows:

| | |
|---|---|
| Filename: | 2-step.txt |
| Size: | 22,817 bytes |
| Date Created: | Jul. 31, 2001 |

The computer program listing appendix is hereby expressly incorporated by reference in the present application.

FIELD OF THE INVENTION

The present invention relates broadly to microscopes, more particularly to a method and apparatus for supplying power to a source of illumination in a microscope, and, even more particularly, to a method and apparatus for gradually supplying power to a source of illumination in a microscope using pulse width modulation to reduce stress on the illumination filament and preserve life of the illumination source.

BACKGROUND OF THE INVENTION

Microscopes use various types of illumination sources to provide the necessary light to illuminate the specimen being examined. Many different factors affect the life of these illumination sources, including the amount of time that the source is energized. Another factor that directly affects illumination source life is the induced stress on a cold filament caused by cold starting at full rated potential. Such full rated potential cold starting can cause deterioration of the filament structure and can lead to premature failure. While various methods for soft-starting illumination sources have been developed, existing methods control the rate of rise of the potential across an illumination source with passive/analog components. Although electronic circuits with passive components can reduce the deterioration process, a method of digitally controlling the turn-on time for a source of illumination would offer many advantages over other methods. Heretofore, such a digital method has not been known in the art.

Thus, it is seen that there is a longfelt need for a method and apparatus for gradually supplying power digitally to an illumination source in a microscope.

SUMMARY OF THE INVENTION

The invention broadly comprises a method and apparatus for gradually supplying power to a source of illumination in a microscope. The apparatus includes a power transistor operatively arranged to provide a varying applied voltage to the source of illumination, and means for biasing the power transistor with a pulse width modulated signal to incrementally increase the applied voltage to the source of illumination in a plurality of discrete steps. The method comprises gradually supplying power to a source of illumination in a microscope by biasing a power transistor with a pulse width modulated signal to incrementally increase the applied voltage to the source of illumination in a plurality of discrete steps.

A general object of the invention is to provide a method and apparatus for gradually supplying power to a source of illumination in a microscope by biasing a power transistor with a pulse width modulated signal to incrementally increase the applied voltage to the source of illumination in a plurality of discrete steps.

Another object of the invention is to provide a method and apparatus for supplying power to a source of illumination in a microscope which preserves source filament life.

Still another object of the invention is to provide a method and apparatus for supplying power to a source of illumination in a microscope which reduces stress induced on a source filament and prevents premature failure of the light source.

These and other objects, features and advantages of the present invention will become readily apparent to those having ordinary skill in the art from a reading and study of the following detailed description of the invention, in view of the drawing and appended claims.

BRIEF DESCRIPTION OF THE DRAWING

The nature and mode of operation of the present invention will now be more fully described in the following detailed description of the invention taken with the accompanying drawing figures, in which.

DESCRIPTION OF THE PREFERRED EMBODIMENT

At the outset, it should be appreciated that like reference numbers on different drawing views represent identical circuit/structural elements of the invention. It should also be appreciated that the following definitions are intended as an aid in understanding the invention and interpreting the claims:

Illumination Source: includes any source of illumination used in a microscope, including but not limited to incandescent light bulbs (Halogen, Tungsten, etc.).

Varying: the term "varying" is meant to mean that the applied voltage changes, i.e., gradually increases. In a preferred embodiment, the applied voltage varies in incrementally increasing discrete steps, although the term varying is intended to broadly mean any type or magnitude of changing applied voltage.

Figure 1:
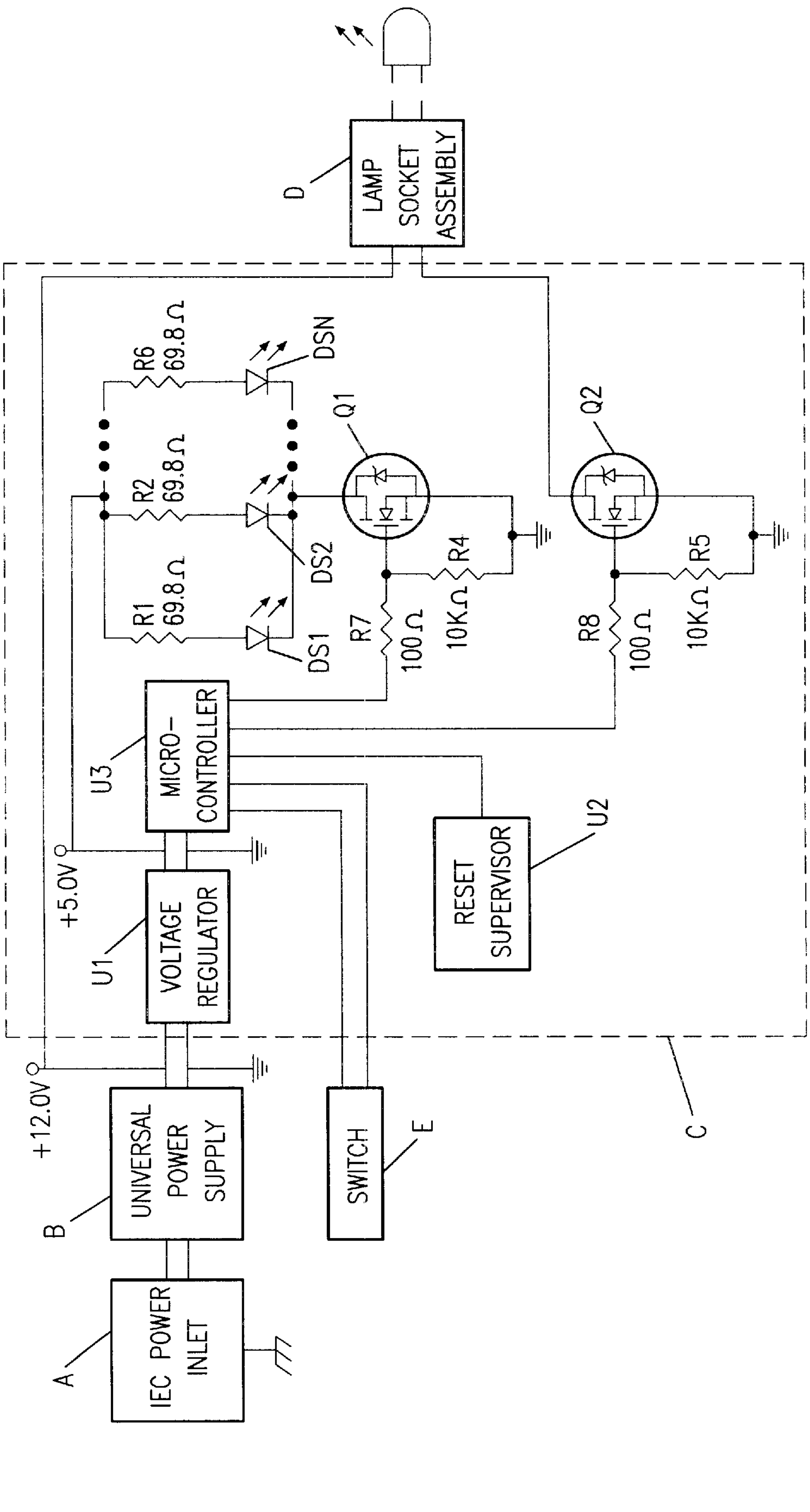
FIG. 1 is a block diagram of the electrical circuit of the present invention.

Referring now to the drawings, FIG. 1 is a schematic block diagram of a preferred embodiment of the electronic system of the invention for controlling a microscope. Component A is an International Electrotechnical Commission (IEC) style appliance coupler with dual-pole fuse holders used to accept any IEC-60320-1 style power cord. Component B is a universal power supply. Component C is the main controller printed circuit board which includes a voltage regulator U1 (LM340T-5.0 or equivalent), microcontroller U3 (PIC16C54C-04P(18) or equivalent), reset supervisor U2 (MCP100-460DI/TO or equivalent), multiple light emitting diodes (DS1–DSN), two MOSFETs (Q1 & Q2)

(IRLZ44N or equivalent), and various resistors and capacitors as shown in the detailed electronic schematic diagram of FIG. 2.

An input power signal in the range from 100–240 VAC +/−10%, 50/60 Hz is applied to the universal power supply via the appliance coupler, an output voltage of 12.0 VDC is transferred from the output of the universal power supply to the input of U1 and the connector for lamp socket assembly D on the main controller printed circuit board. U1 steps down the 12.0 VDC signal to a 5.0 VDC signal that powers all the integrated circuits within main board C.

Upon powering the main board, U2 holds U3 in a reset state for a preconditioning period of time to allow U3's crystal to stabilize. After the preconditioning period of time, U3 begins operation. The first routine executed by U3 is an initialization routine that configures the internal registers for U3 and causes U3 to set external devices in a predefined state. Subsequently, the system is designed to place Q1 and Q2 in an off-state by sending a logic-low (0.0 VDC) signal to each gate. Therefore, after initialization, all the sources of illumination are in the off-state or powered down.

After the initialization routine, the main routine is executed. During the main routine two major events are monitored. First, switch E is polled for activity and time is monitored from the last activation of switch E. If no activity on switch E is detected after a predetermined period of time, all the sources of illumination are turned off. Any activity on switch E will reset the registers tracking time within U3 to zero.

Each time the switch is pressed U3 cycles through the following four events. First, the source of illumination in the lamp socket assembly is turned on. Second, the LEDs are turned on while the source of illumination in the lamp socket assembly is turned off. Third, while the LEDs are left in the on-state, the source of illumination in the lamp socket assembly is turned on. Fourth, all the sources of illumination are turned off. The process of digitally soft-starting the source of illumination is executed each time the sequence in the cycle requires turning on the source of illumination.

Figure 4:
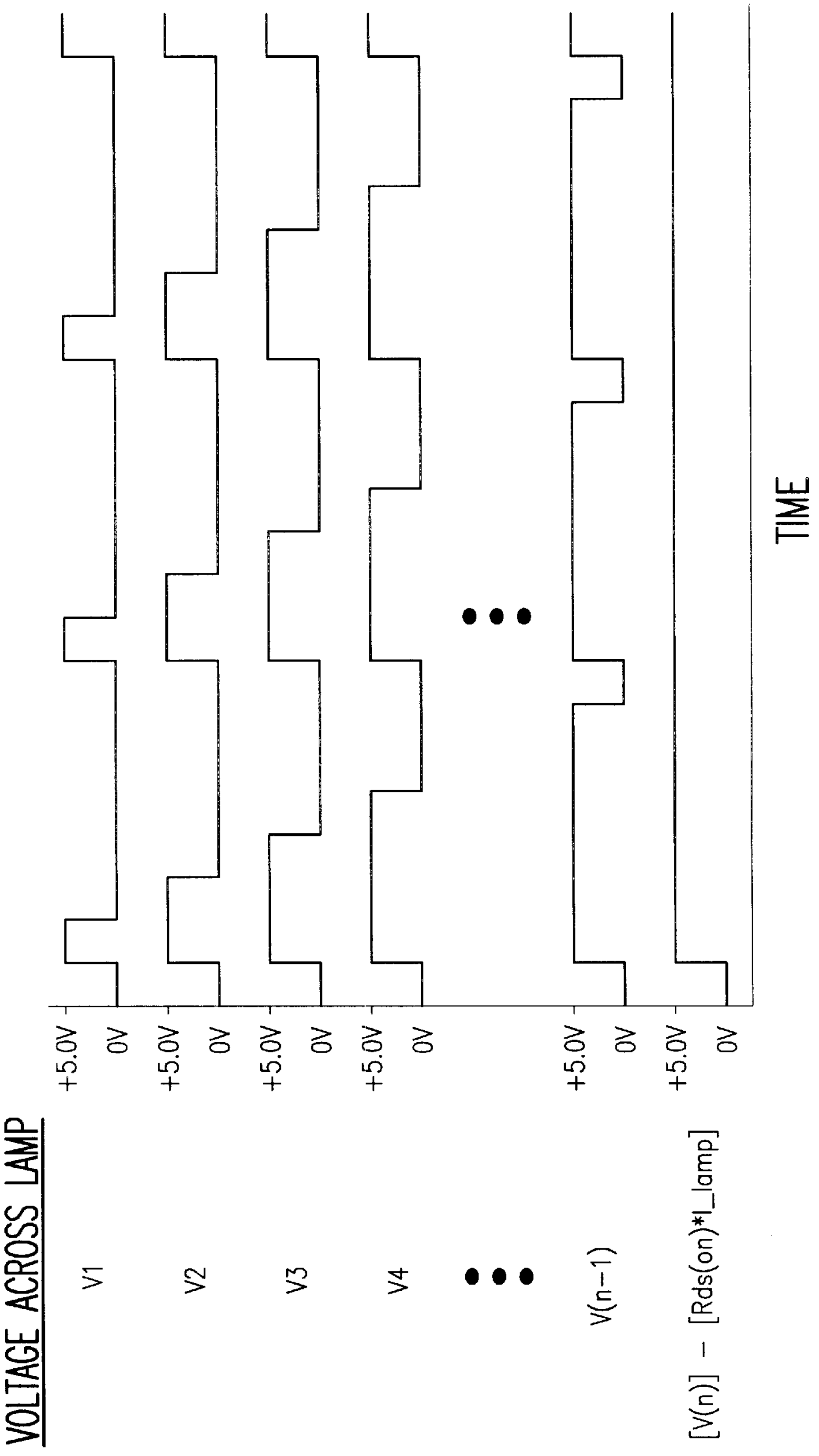

During the process of soft-starting, a pulse-train (square-wave) is sent out of U3 to the gate input of Q2 causing the voltage to slowly ramp-up from 0.0 VDC to the maximum potential supplied by the power supply across the source of illumination. The number of steps to reach the final steady-state voltage is fixed in a software program, included herein on compact disc. However, it should be appreciated that one having ordinary skill in the art can easily alter the program to affect any number of steps and the voltage increments at each step. A representative pulse-train square wave signal and resulting applied voltage is illustrated in FIG. 4. The first applied voltage, V1, is applied to the lamp for a time $t_1$. The pulse width modulation is then adjusted to provide a voltage, V2, to the lamp for a time $2xt_1$. This process of gradually increasing the time period for application of the applied voltage continues until full applied voltage is attained. It should be appreciated that the control scheme of the present invention is suitable for use with microscopes with one or more sources, and types of illumination. For example, the scheme is applicable and suitable for soft-starting halogen, tungsten and other types of illumination sources, individually or in combination.

With a 20 MHz crystal oscillator driving U3, the pulse-train starts with a high pulse-width of 600 nS (on-time) in low pulse-width of 65.4 $\mu$S (low-time) giving a constant frequency of 15.152 kHz. Subsequently, one can program a different constant frequency and set the starting voltage applied to the source of illumination. After a predefined delay period that is software programmable and adjustable, the on-time is increased by 600 nS any off-time is decreased by 600 nS maintaining a constant frequency. The process of increasing the on-time and decreasing the off-time is continued until the predefined number of steps is reached at which the gate of Q2 is driven with a steady-state 5.0 VDC signal. With a 5.0 VDC apply to the gate of Q2, the full potential from the power supply, minus the voltage drop across Q2, is applied across the source of illumination.

The total soft-start time-period to achieve full potential across the illumination source is controlled by the number of steps, frequency of the square-wave, delay at each step where the pulse-trained is at a constant pulse-width, and some overhead code resulting from sequential branching within the soft-start routine. Since the number of steps, frequency of the square-wave, and delay at each step is fully programmable, the soft-start time-period can be set to any rate as a function of the crystal oscillator driving U3. Relative applied voltage (V1, V2, V3, . . . [V9N)]–[Rds(on)*I_lamp]) to the lamp versus time for various programmed time periods is illustrated in FIG. 4.

Figure 2A:
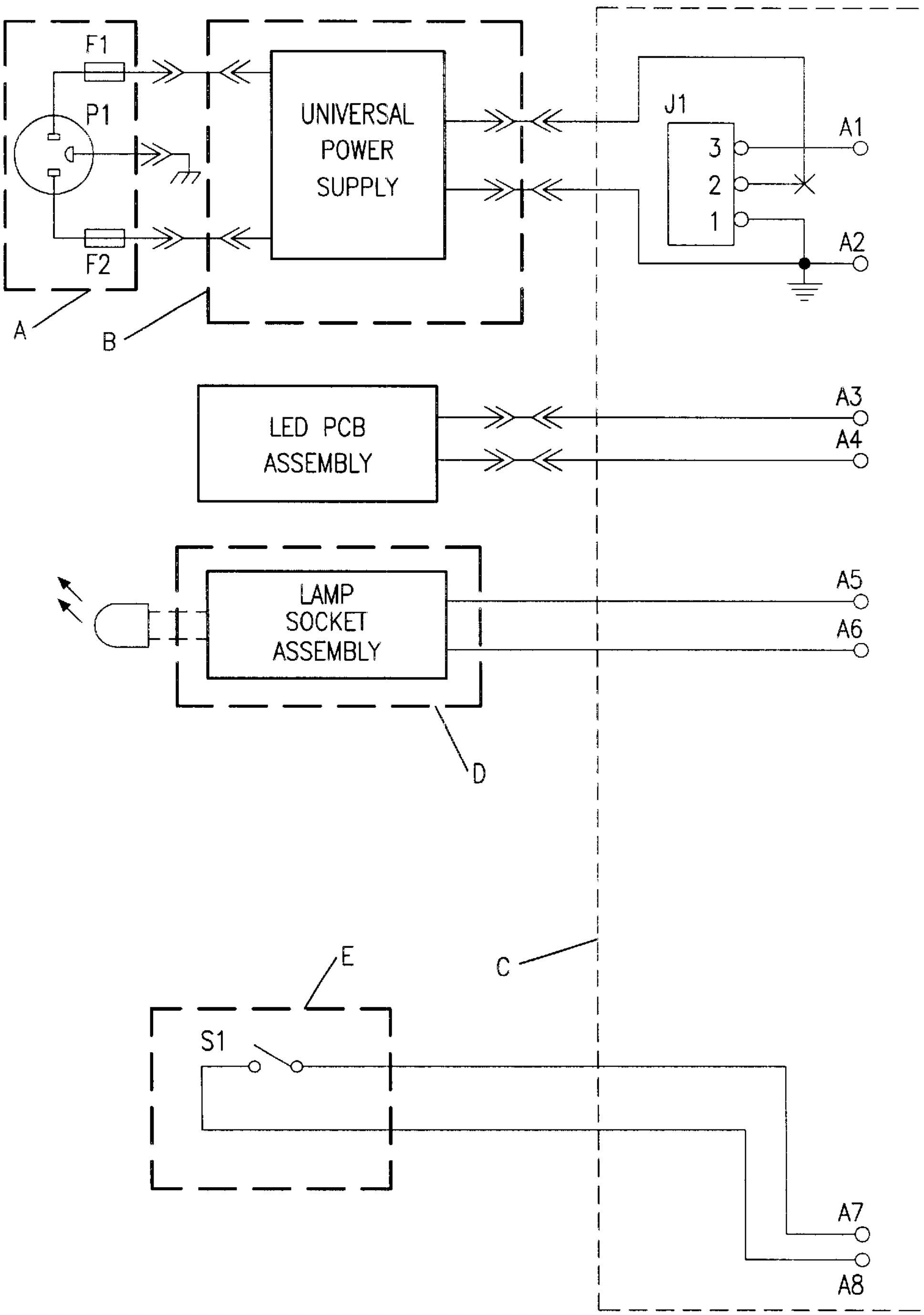
FIGS. 2A, 2B and 2C comprise a detailed electronic schematic diagram of the circuit of the present invention.
Figure 2B:
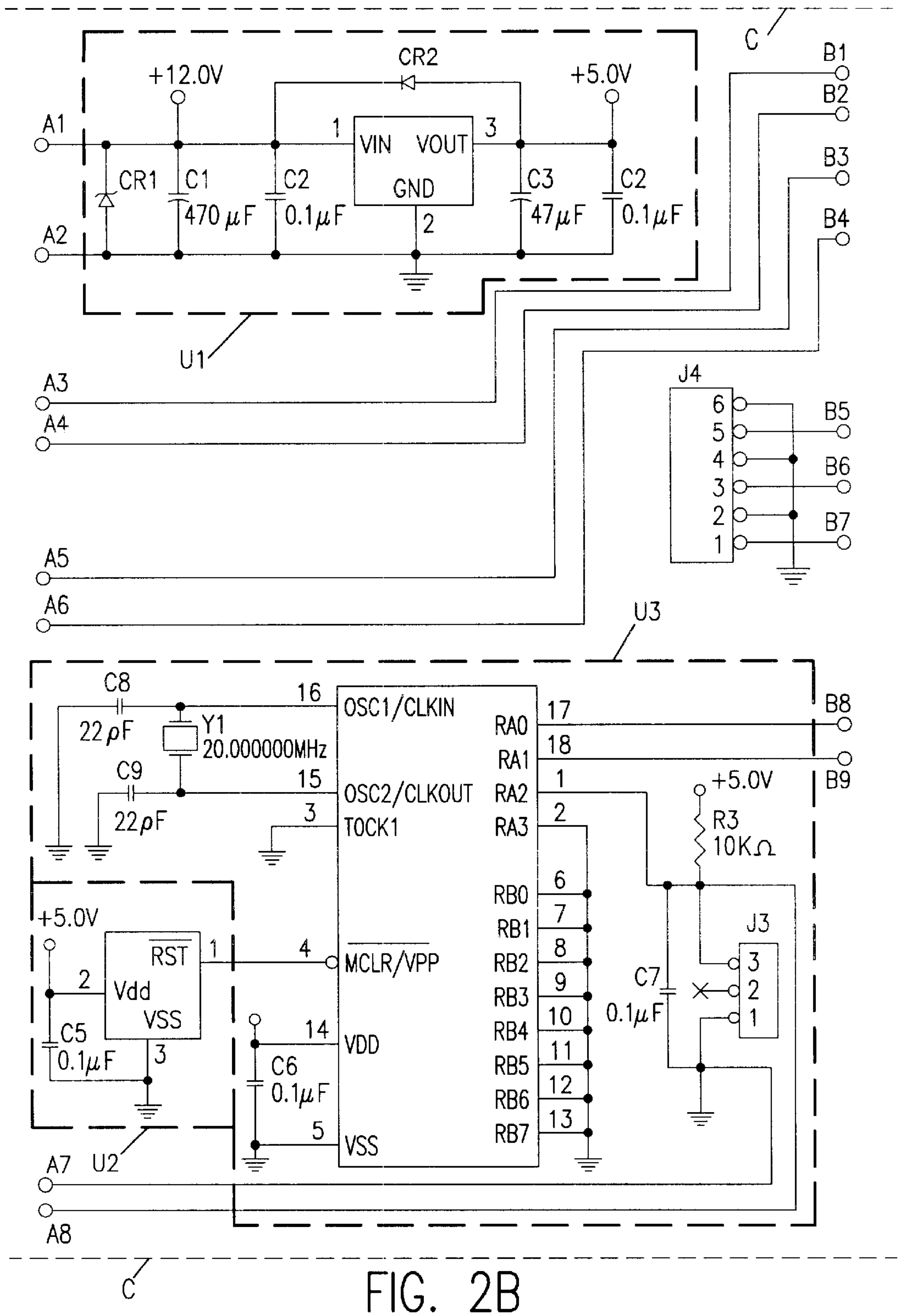
Figure 2C:
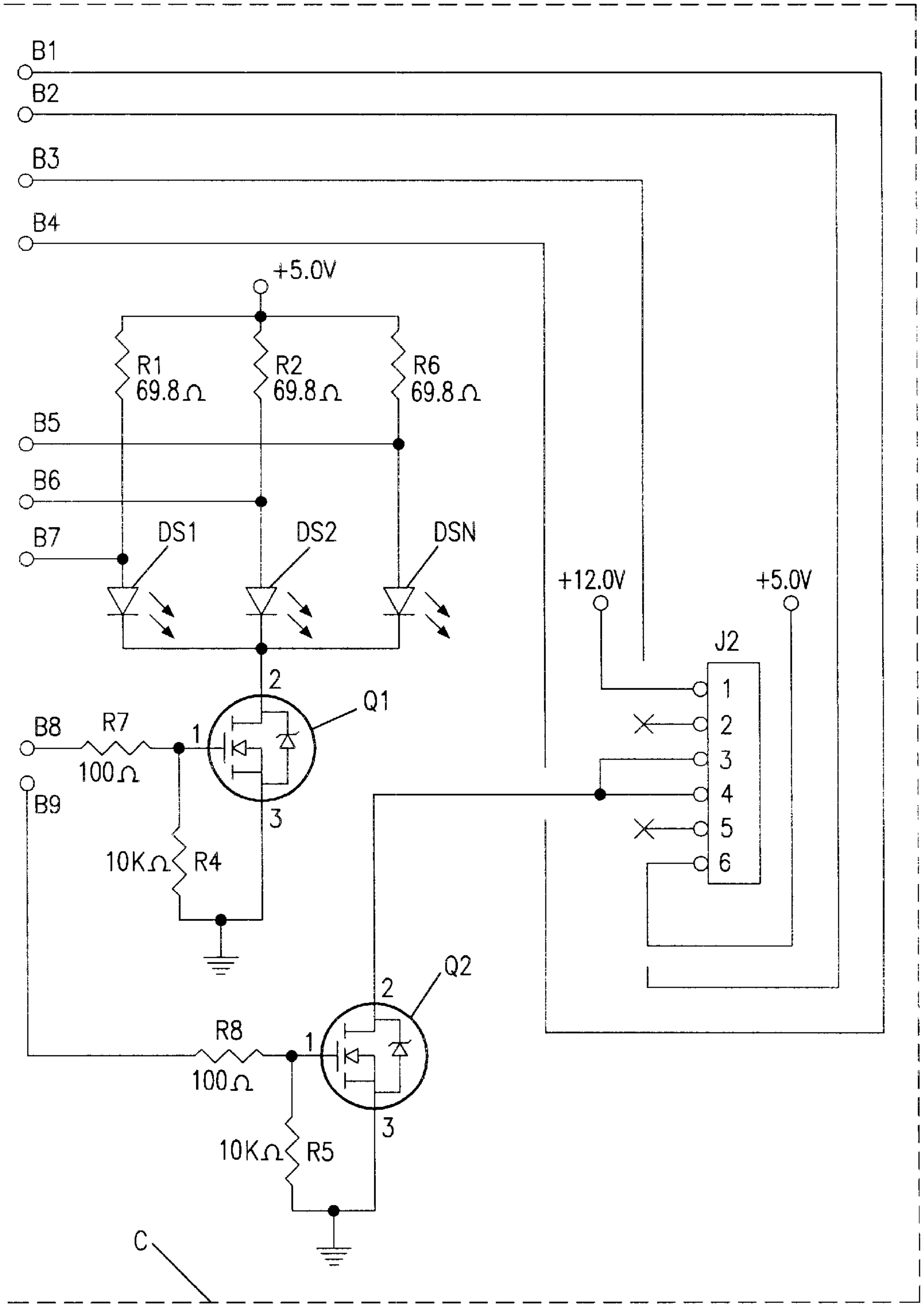
Figure 3:
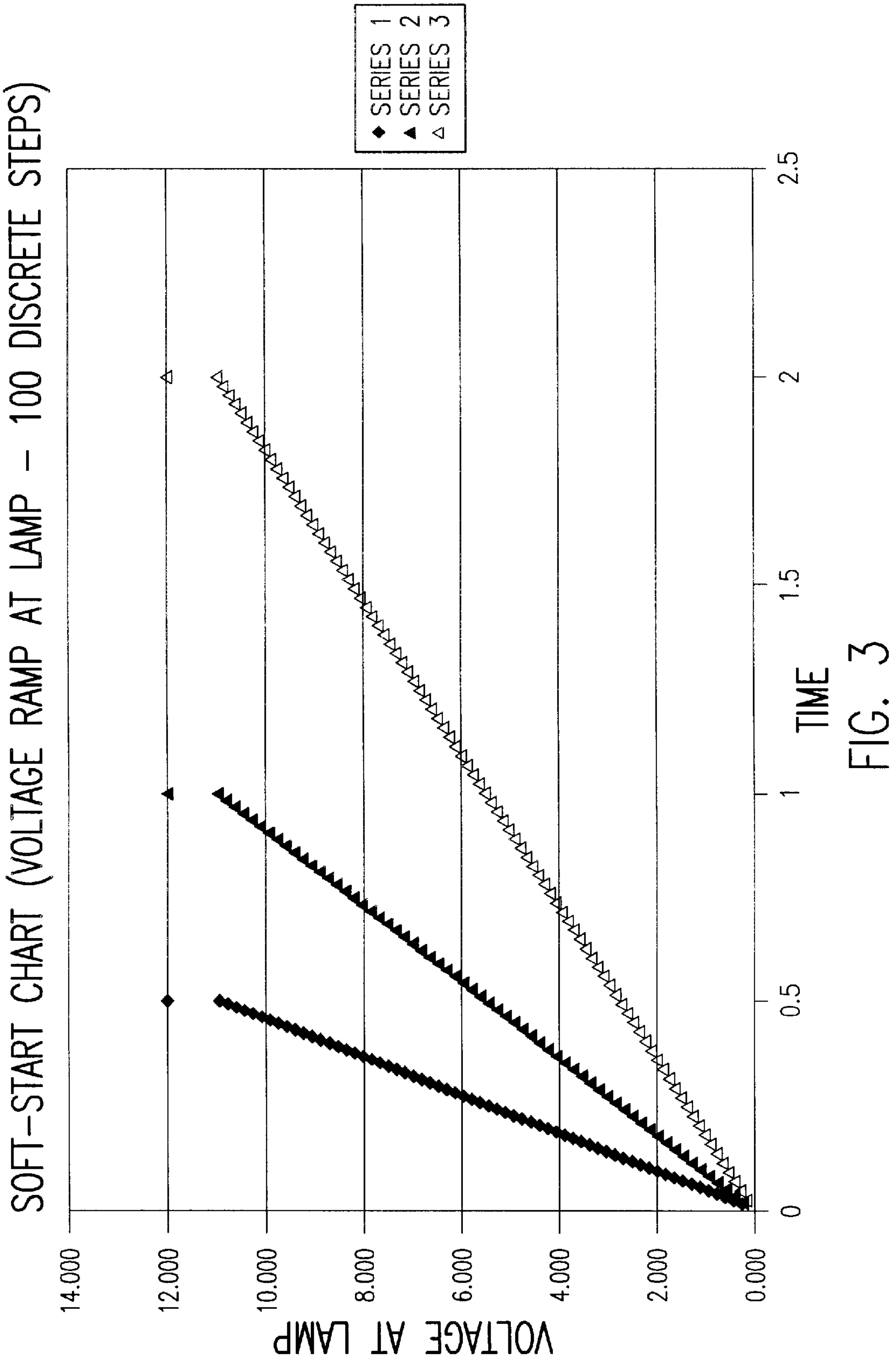
FIG. 3 is a chart illustrating the relationship between applied voltage versus time for three different pulse width modulation schemes; and, FIG. 4 is an illustration of applied voltage across a lamp versus time for a particular pulse width modulation scheme, illustrating gradual power-up of the lamp.

To enable one having ordinary skill in the art to make the invention, a detailed electronic schematic diagram is provided in FIGS. 2A, 2B and 2C, showing all circuit elements, their values, and interconnections. These three drawings figures together comprise the entire drive and control circuit of the present invention. Interconnections of lead lines are illustrated by jumpers A1, A2, . . . B1, B2, . . . , etc. For example, the lead line that terminates in jumper A1 on FIG. 2A connects to the same lead line on FIG. 2B at jumper A1, etc.

Thus, it is seen that the objects of the invention are efficiently obtained, although changes and modifications to the invention can be readily appreciated by those having ordinary skill in the art, and these changes and modifications are intended to be within the spirit and scope of the invention as claimed.

What is claimed is:

1. An apparatus for gradually supplying power to a source of illumination in a microscope, comprising:

a power supply operatively arranged to provide a first voltage;

a power transistor operatively coupled to said power supply and operatively arranged to provide a varying applied voltage to said source of illumination; and, means for biasing said power transistor with a pulse width modulated signal to incrementally increase said applied voltage to said source of illumination in a plurality of discrete steps until said applied voltage approximates said first voltage; and, wherein said means for biasing said power transistor with a pulse width modulated signal causes said power transistor to incrementally increase said applied voltage to said source of illumination in a plurality of discrete steps until said applied voltage equals said first voltage, less a voltage drop across said power transistor.

2. An apparatus for gradually supplying power to a source of illumination in a microscope, comprising:

a power transistor operatively arranged to provide a varying applied voltage to said source of illumination; and, means for biasing said power transistor with a pulse width modulated signal to incrementally increase said applied voltage to said source of illumination in a plurality of discrete steps; and, wherein said means for biasing said power transistor with a pulse width modulated signal ramps up the applied voltage across said source of illumination in even increments at a constant frequency with a duty cycle that starts at 0% and ends at 90% before maximum rated applied voltage is applied across said source of illumination.

3. The apparatus recited in claim 1 wherein said pulse width modulated signal is provided by a microprocessor.

4. The apparatus recited in claim 1 wherein said power transistor is biased with a digital signal.

5. The apparatus recited in claim 4 wherein said digital signal is a square wave.

6. The apparatus recited in claim 2 wherein said pulse width modulated signal is provided by a microprocessor.

7. The apparatus recited in claim 2 wherein said power transistor is biased with a digital signal.

8. The apparatus recited in claim 7 wherein said digital signal is a square wave.

9. A method for gradually supplying power to a source of illumination in a microscope, said method comprising the steps of:

providing a first voltage through a operatively arranged power supply;

providing a transistor operatively coupled to said power supply and operatively arranged to provide a varying applied voltage to said source of illumination; and, biasing said power transistor with a pulse width modulated signal to incrementally increase said applied voltage to said source of illumination in a plurality of discrete steps until said applied voltage approximates said first voltage; and, wherein said biasing of said power transistor with a pulse width modulated signal causes said power transistor to incrementally increase said applied voltage to said source of illumination in a plurality of discrete steps until said applied voltage equals said first voltage, less a voltage drop across said power transistor.

10. The method recited in claim 9 wherein said pulse width modulated signal is a square wave.

11. The method recited in claim 10 wherein said square wave is operatively arranged to have an incrementally increasing duty cycle.

12. A method for gradually supplying power to a source of illumination in a microscope, said method comprising the steps of:

providing a varying applied voltage to said source of illumination through a operatively arranged power transistor; and, biasing said power transistor with a pulse width modulated signal to incrementally increase said applied voltage to said source of illumination in a plurality of discrete steps; and, wherein said biasing of said power transistor with a pulse width modulated signal ramps up the applied voltage across said source of illumination in even increments at a constant frequency with a duty cycle that starts at 0% and ends at 90% before maximum rated applied voltage is applied across said source of illumination.

13. The method recited in claim 12 wherein said pulse width modulated signal is a square wave.

* * * * *